(12) United States Patent
Ochiai et al.

(10) Patent No.: US 7,838,051 B2
(45) Date of Patent: *Nov. 23, 2010

(54) METHOD FOR MANUFACTURE OF POLYPHENOLS BY USING SEEDS AS STARTING MATERIAL

(75) Inventors: Koji Ochiai, Napa, CA (US); Nobuko Ueda, Napa, CA (US)

(73) Assignee: Indivi Wine, Ltd., Okazaki-Shi, Aichi (JP)

( * ) Notice: Subject to any disclaimer, the term of this patent is extended or adjusted under 35 U.S.C. 154(b) by 143 days.

This patent is subject to a terminal disclaimer.

(21) Appl. No.: 11/852,722

(22) Filed: Sep. 10, 2007

(65) Prior Publication Data

US 2008/0020113 A1    Jan. 24, 2008

Related U.S. Application Data

(62) Division of application No. 11/246,442, filed on Oct. 6, 2005, now Pat. No. 7,288,272.

(30) Foreign Application Priority Data

Jan. 7, 2005    (JP) .............................. 2005-002002

(51) Int. Cl.
  *A61K 36/87* (2006.01)
(52) U.S. Cl. ..................................................... 424/766
(58) Field of Classification Search ........................ None
   See application file for complete search history.

(56) References Cited

U.S. PATENT DOCUMENTS 5,773,262 A    6/1998   Ariga et al.
6,544,581 B1 *  4/2003  Shrikhande et al. ......... 426/655
2005/0191268 A1  9/2005  Henry et al.

FOREIGN PATENT DOCUMENTS

JP    2001-158739    12/2001

OTHER PUBLICATIONS

Tomoya Takahashi, Proanthocyanidins from Grape Seeds Promote Proliferation of Mouse Hair Follicle Cells In vitro and Convert Hair Cycle in vivo, Aeta Derm Venereco (Stockh) 1998: 78; 428-432.

* cited by examiner

*Primary Examiner*—Patricia Leith
*Assistant Examiner*—Melenie McCormick
(74) *Attorney, Agent, or Firm*—Glen L. Gross, Esq.; Shiesinger, Arkwright & Garvey, LLP

(57) ABSTRACT

To provide a method for the manufacture of polyphenols that enables industrial manufacture of polyphenols containing water-soluble proanthocyanidins from grape seeds. The seeds of grape berries dried after squeezing out the juice are separated into grape seeds and peel with a separation apparatus, and the grape seeds are stirred in a washing machine to remove contamination thoroughly. The grape seeds are charged into a boiling kettle and heated for the prescribed time at the prescribed temperature. Then, germination is induced in a curing kettle maintained at the prescribed temperature preferred for the germination. The grape seeds in which germination or germination and differentiation have advanced are crushed, mixed with water to obtain an emulsified state, and a salt is added, if desired. After a known desalting treatment has been conducted with respect to an aqueous solution portion, water is evaporated with a vacuum apparatus to obtain polyphenols comprising proanthocyanidins converted to a water soluble form.

6 Claims, No Drawings

METHOD FOR MANUFACTURE OF POLYPHENOLS BY USING SEEDS AS STARTING MATERIAL

CROSS REFERENCE TO RELATED APPLICATION

This application is a divisional application of U.S. application Ser. No. 11/246,442, filed on Oct. 6, 2005 now U.S. Pat. No. 7,288,272, which claims priority to Japanese Application No.: JP2005-002002 filed on Jan. 7, 2005, both of which are incorporated, in their entirety, herein by reference.

BACKGROUND OF THE INVENTION

1. Field of the Invention

The present invention relates to a method for the manufacture of polyphenols by using grape seeds as a starting material, this method designed to obtain polyphenols comprising proanthocyanidins converted to a water soluble form.

2. Background of the Invention

Because polyphenols contained in plants produce an antioxidation effect, they have been used in a large variety of food products, drugs, and cosmetics. Proanthocyanidins are polyphenols that produce an especially strong antioxidation effect. As described in Patent Reference 1, proanthocyanidins are polyphenols contained in a large amount in plants such as grapes, apples, persimmon, and pine, and because of their especially strong antioxidation effect, they are used for a variety of applications described, for example, in Para. Nos. 0031-0034 of Patent Reference 1.

[Patent Reference 1] Japanese Patent Application Laid-open No. 2001-158739.

SUMMARY OF INVENTION

Problems Addressed by the Invention

However, in the form in which proanthocyanidins are most generally present in the natural world, they are most often insoluble in water. For example, in grape berries, though proanthocyanidins are contained in peel, flesh and seeds, they are all insoluble in water. For this reason, the field of application for proanthocyanidins tends to be relatively limited. For example, when they are used in cosmetics, though they can be contained in creams, they cannot be contained in cosmetic tonics containing no added alcohol. Furthermore, when used orally (food etc.), because water-insoluble proanthocyanidins are difficult to absorb, the use thereof is avoided and other polyphenols that are readily soluble in water are widely used despite their poor antioxidation effect. Therefore, though proanthocyanidins are examples of ingredients actually contained in food products and the like, as long as they are water-insoluble proanthocyanidins, a sufficient antioxidation effect cannot be demonstrated. Some plants contain water-soluble proanthocyanidins, but they cannot ensure stable supply of large amounts of water-soluble proanthocyanidins, and there is need for industrial technology capable of guaranteeing such a supply.

The present invention focuses attention on the problems in the conventional technology described above. An object thereof is to provide a method for the manufacture of polyphenols that enables industrial manufacture of polyphenols containing water-soluble proanthocyanidins from grape seeds.

DETAILED DESCRIPTION OF INVENTION

Means to Resolve the Problems

In order to resolve the above-described problems, the invention of claim 1 provides a method for the manufacture of polyphenols comprising a drying step of drying grape seeds after juice removal in which the grape seeds are dried alone or with seed coat, a heating step of heating the grape seeds dried in the drying step in a temperature range above the temperature optimum for germination and under heating conditions such that cause no thermal transformation of proteins present in the grape seeds, a hydration step of hydrating the grape seeds simultaneously with the heating step or after the heating step, and a germination induction step of germinating or germinating and differentiating the grape seeds, which were heated in the heating step and hydrated in the hydration step, in a temperature range optimum for germination, wherein a polyphenol comprising a proanthocyanidin converted to a water-soluble form is extracted from the grape seeds after the germination induction step.

With the invention of claim 2, in addition to the features of the invention of claim 1, the index of the degree of dryness in the drying step is the water content ratio of the grape seeds, and the target value of the water content ratio is 9-12%.

With the invention of claim 3, in addition to the features of the invention of claim 1 or 2, the index of water content in the hydration step is the water content ratio of the grape seeds, and the target value of the water content ratio is 17% or more.

With the invention of claim 4, in addition to the features of any claim of claims 1 to 3, the temperature range above the temperature optimum for germination of the grape seeds is 50-70° C.

Employing the above-described features makes it possible to induce germination or germination and differentiation of grape seeds, and to extract polyphenols comprising proanthocyanidins converted to a water soluble form.

Usually, proanthocyanidins contained in grape seeds are insoluble in water. Therefore, they have to be converted into water-soluble proanthocyanidins. For this purpose, the inventors, first, have subjected the grape seeds after juice removal to drying in which the grape seeds are dried alone or with seed coats. Owing to the drying, the content ratio of water in the grape seeds is decreased and a transition is made to a type of dormant state.

The meaning of drying will be described below based on plant physiology. In the drying step, juice is removed and the internal seeds are exposed to air and dried naturally or forcibly, thereby differentiating the starch present in the grape seeds to accumulated starch and differentiating the germination-related substances. The drying not only releases free water of the seeds to the outside of the seed body, but at the same time also enhances the release of the bonded water to the outside of seed body by the differentiation of those substances of the seeds themselves by external stimulation, i.e., drying. For example, even when seeds that were directly taken from ripe grape berries are planted in a temperature range optimum for germination, the germination ratio is very low (about 2-3% for the grapes). This is due to the fact that physiological conditions required for germination have not been fully arranged. On the other hand, subjecting the grape seeds to the drying step provides a necessary condition for germination. It does not mean that grapes that passed the dormant stage will necessarily demonstrate rapid increase in germination ratio, as certain plants do after passing the dormant stage. However, the germination ratio is difficult to increase if the grape seeds have not passed at least the drying step.

As drying advances, the grape seeds make a transition to a type of dormant state. In the present invention, the grape seeds may be in a dormant state or a state close to a dormant state (theoretically, differentiation to accumulated starch and differentiation of germination-related substances may be completed). The water content ratio may be an indicator of whether this state has been attained or not. According to the idea of the present invention, the preferred water content ratio that is the target of drying is 9-12%, more preferably 9-11%. The water content ratio of seeds present in grape berries is generally about 14%, regardless of the kind of grapes. Grape seeds do not have a water content ratio of more than 14%, unless they are germinated and differentiated to a physiologically allowed limit (in other words, as long as they are alive).

Furthermore, because a certain time is required for the differentiation of grape seeds, from the standpoint of germination ratio increase, it is preferred that the drying step be implemented slowly over many days (several weeks to several months) rather than within a short interval.

For example, dregs (the so-called juice pomace) remaining after squeezing out the juice for the fabrication of juice or making a white wine or dregs (the so-called wine pomace) appearing in the process of making a red wine can be used as means for naturally drying the seeds. If those dregs are open-air stored for a fixed period, dried, and used as a starting material, then gradual drying is conducted, as described hereinabove, and cost can be advantageously reduced. Furthermore, another effect that can be expected is that open-air storage causes decay of seed coats, thereby facilitating subsequent separation of seeds and seed coats in the below-described washing process. A large electric fan or heater can be also considered as drying means for forcible drying, but in this case, too, the germination ratio can be increased by allowing the seeds to stay after drying for several weeks to several months, as described above, rather than making an immediate transition to the next step.

Furthermore, after the above-described drying step, the inventors have heated the grape seeds in a temperature range above the temperature optimum for germination and under heating conditions such that cause no thermal transformation of proteins present in the grape seeds.

The germination ratio has been planned to be greatly increased by intensely heating the grape seeds that were made dormant by drying. At this stage, seed coats are preferable removed from the grape seeds, but they may be also left intact.

Here, "the heating temperature optimum for germination of grape seeds" is considered to be about 20-45° C., more preferably 23-40° C. Furthermore, "the temperature range above the heating conditions causing no thermal transformation of proteins present in the grape seeds" does not necessarily mean that a high temperature is excluded. Because the grape seeds are covered with seed coats, heat does not directly penetrate into the seeds. It means that the treatment can be conducted at a high temperature (for example 65-70° C.) causing transformation of proteins, provided that the processing time is short. Conversely, long-term heating can be employed if the temperature is comparatively low (for example, about 50° C.). In some cases heating can be conducted at a temperature of 100° C. or higher in an evaporation kettle or the like. The temperature and heating time are inversely proportional to each other. However, heating is a step completed within a much shorter time that the drying step and the subsequent germination induction step. In other words, it is also a step in which intense heating is conducted within a short time.

The effect of such a heating step is that germination is enhanced by subjecting the dormant grape seeds to strong external stimulation. The grape seeds make a transition from the dormant state to the germination and differentiation step.

Here, the inventors have conducted hydration of the grape seeds simultaneously with the heating step or after the heating step. This is because the heating caused the grape seeds to make a transition from the dormant state to the germination and differentiation state and the grape seeds absorb a large amount of water as the germination and differentiation begin. It goes without saying that this does not exclude a process of continuous hydration in the subsequent germination induction step.

The water content ratio increased by the germination and differentiation is preferably at least 17% or more. In other words, whether or not the grape seeds have made a transition from the dormant state to the germination and differentiation step can be checked by verifying that the water content ratio is 17% or more. In this case, if the seeds have not been germinated and differentiated, they cannot be hydrated to a water content ratio of more than the aforementioned 14% even if immersed in water. A germination enhancement hormone can be added after the heating step.

Then, the inventors have conducted germination induction by curing the grape seeds that have been sufficiently hydrated by curing in a temperature range optimum for germination. Germination or germination and differentiation of the grape seeds is thereby enhanced. In the present invention, because the grape seeds passed through the above-described steps, the germination ratio can be found to be significantly increased by comparison with the conventional processes. Under certain conditions, a germination ratio of 95% and higher is observed. From the standpoint of plant physiology, because of active action of this germination and differentiation, modification of polyphenols present in the grape seeds was confirmed. Presently about 30 types of polyphenols present in the grape seeds have been identified, but in the present invention, main attention is focused on modification of proanthocyanidins. Glycosidation of sugars following the germination and differentiation of grape seeds results in the development of polarity, and a transformation is made from water-insoluble proanthocyanidins to water-soluble ones.

BEST MODE FOR CARRYING-OUT THE INVENTION

A method for the manufacture of polyphenols by using grape seeds as a starting material will be described below.

(Manufacturing Means)

First, an example of means for industrially extracting polyphenols that were made water soluble from grape seeds will be explained. Only one example of the apparatus used in each step is described, but the below-described apparatuses are not limiting, provided that the processing of each step can be executed.

Wine pomace and juice pomace are the starting materials that are the easiest to be procured in large amounts. Those starting materials are used after allowing them to stay under conditions facilitating drying over the prescribed period after squeezing out the juice, so that the water content ratio thereof is decreased. If those starting materials are not subjected even to the usual treatment, they have a very poor germination ratio. In particular the germination ratio of the wine pomace is poorer than that of the juice pomace, which is apparently due to a germination inhibition action of ethyl alcohol.

(Sorting and Washing Step)

The object of this step is to obtain individually washed grape seeds.

Grape seeds and peels are sorted with a sorting apparatus equipped with a punching metal and then the classified grape seeds are stirred in a washing machine to remove contamination thoroughly.

(Heating Step)

The grape seeds obtained in the above-described sorting and washing step are charged into a boiling kettle. They are heated for the prescribed time at a prescribed temperature. As a result, the grape seeds emerge from the dormant state.

(Germination Induction Step)

The grape seeds heated in the heating step are taken out and subjected to germination induction in a curing kettle held at the prescribed preferred germination temperature. Germination and differentiation of the grape seeds is initiated in the curing kettle and the water content ratio increases rapidly.

(Extraction Step)

Grape seeds whose germination or germination and differentiation have advanced in the above-described step are charged into a crushing apparatus, crushed, mixed with water and converted into an emulsion. In this step, a salt such as table salt or ammonium sulfate may be added to precipitate (salt out) proteins and dissolve (salt in) water-insoluble substances.

(Filtration Step)

Other components are further extracted from the precipitated layer with an organic solvent (ethyl alcohol and the like). After the water-soluble portion has been subjected to a known desalting treatment, water is evaporated with a vacuum apparatus and polyphenols comprising proanthocyanidins converted to a water soluble form in a concentrated state is obtained. Water-insoluble components are further extracted from the residue with an organic solvent.

The results obtained in simulating the process of obtaining water-soluble polyphenols in accordance with the present invention will be explained below as working examples.

Working Example 1

1) Simulation Conditions

A total of 25 g of seeds were selected for use from grape seeds (Riesling type: water content 9.5-11.0) derived from juice pomace that was open-air stored for 6 months. After washing in running water, the seeds were immersed in 100 ppm antiformin solution (antiformin is a bactericide) at 50° and incubated for 1 h. After 1 h, the seeds were taken out from the solution, immersed into antiformin solution at 40° and incubated for 4 h. The seeds were then taken out of the solution and washed with distilled water. Water was thereafter removed with soft paper. The seeds were then planted into a sponge containing 10 ppm antiformin solution and allowed to stay at 24° C. The temperature of 24° C. is the optimum germination temperature for grape seeds, but in order to enhance water absorption of strong seeds, a germination preparation period of placing in a rather high-temperature zone such as 40° C. was set prior to the optimum temperature. A 10 ppm antiformin solution was sprinkled for 12 h to prevent the seeds from drying.

2) Extraction of Germinated Seeds

At a timing of 24 h (1 day), 48 h (2 days), 96 h (4 days), and 168 h (7 days), respectively, 100 seeds (4.12 g) were selected, 10 mL of buffer solution (distilled water) was added, and the seeds were crushed with a mortar and a pestle. The product was centrifugally separated for 15 min at 10,000×g and the supernatant thereof was used as a sample.

3) Measurement of Water-soluble Polyphenols

The absorbance at each wavelength of 220 nm, 280 nm, and 550 nm was measured with a spectrophotometer with respect to the sample. At a wavelength of 550 nm, measurements were conducted by coloring the sample by adding 0.5 mL of 0.1% iron (III) chloride to 4 mL of the sample liquid. At a wavelength of 220 nm, light absorption specific to amino acids and proteins was observed. At a wavelength of 280 nm, light absorption specific to substances having a benzene ring was observed, and at a wavelength of 550 nm, light absorption specific to substances comprising phenols was observed. If polyphenols are present, light absorption can be observed at both the wavelength of 280 nm and the wavelength of 550 nm.

The amount of polyphenols was determined by titration with a phenol reagent and taking gallic acid as a standard. Furthermore, the samples were obtained by using as starting materials the grape seeds sampled multiple times from different zones of the juice pomace, and an average value was taken for a total of ten measurements conducted by using similarly obtained samples. The results are shown in Table 1.

Furthermore, the presence of polyphenols in the samples was confirmed by the well-known Folin-Ciocalteu reaction. The presence of glycosides was confirmed by the well-known phenol—sulfuric acid method.

TABLE 1

| Wavelength | 1 day | 2 days | 4 days | 7 days |
|---|---|---|---|---|
| A220 | 0.583 | 0.291 | 0.393 | 0.473 |
| A280 | 0.292 | 0.452 | 1.41 | 0.982 |
| A550 | 0.592 | 0.895 | 1.861 | 1.534 |
| Amount of polyphenols (mg/100 mL) | 10.9 | 18.3 | 36.6 | 30.2 |

4) Results

The absorbance at a wavelength of 220 nm reached a maximum in the first day and then changed steadily with repeating moderate fluctuations. In other words, the increase in amino acids and proteins was not confirmed. On the other hand, the absorbance at a wavelength of 280 nm increased significantly with each passing day. In other words, it can be said that the amount of a substance comprising a benzene ring increased. This substance is supposedly a polyphenol, but there remains a possibility that the amount of proteins or amino acids, which are other main ingredients, has increased. For this reason, the absorbance at a wavelength of 550 nm was also measured. As a result, a significant increase was also confirmed at a wavelength of 550 nm. Those results led to a conclusion that the substance whose amount has increased is a polyphenol (there are also amino acids demonstrating light absorption at both the wavelength of 280 nm and the wavelength of 550 nm, but generally they are absent and judging by the amounts, the possibility of them being present is zero).

Furthermore, as was confirmed by using thin-layer chromatography, a distinct reaction was obtained for substances comprising polyphenols and sugars. In other words, a glycoside polyphenol (water-soluble) was confirmed to be present in a comparatively large amount in the sample. Because proanthocyanidins are polyphenols that are most specific for grape seeds and are present therein at a highest ratio, those glycoside polyphenols can be supposed to comprise a large amount of glycosides of proanthocyanidins.

Comparative Example 1

1) Simulation Conditions

A total of 25 g of seeds were selected for use from grape seeds (Riesling type: water content 9.5-11.0) derived from juice pomace that was open-air stored for 6 months. After washing in running water, 100 seeds (4.12 g) were selected, 10 mL of buffer solution (distilled water) was added, and the seeds were crushed with a mortar and a pestle. The product was centrifugally separated for 15 min at 10,000×g and the supernatant thereof was used as a sample. The grape seeds of Comparative Example 1 were not subjected to special treatment for germination and were used directly after washing.

2) Measurement of Water-Soluble Polyphenols

Similar to the above-described Working Example 1, absorbance at each wavelength of 220 nm, 280 nm, and 550 nm was measured with a spectrophotometer.

Furthermore, the amount of polyphenols was determined by titration by using a phenol reagent and taking gallic acid as a standard. Starting materials from different zones similar to those of Working Example 1 were used, a total of ten measurements were conducted and an average value was taken. The results are shown in Table 2.

3) Results

The amount of polyphenol obtained in Comparative Example 1 was about half that obtained after one day for grape seeds of Working Example 1. This polyphenol was inherently soluble in water and showed no increase, as in Working Example 1.

As was confirmed by using thin-layer chromatography, only a slight reaction was obtained with respect to a substance comprising both the polyphenol and sugars. This is because there was no synthesis of glycoside polyphenol accompanying the germination and differentiation. In other words, though a polyphenol (water-soluble) was confirmed to be present in the sample, it was confirmed that almost none of the polyphenol was present as a glycoside polyphenol.

TABLE 2

| Wavelength | |
|---|---|
| A220 | 0.303 |
| A280 | 0.172 |
| A550 | 0.311 |
| Amount of polyphenols (mg/100 mL) | 5.2 |

Comparative Example 2

Working Example 1

1) Simulation Conditions

The residue of the sample used in Working Example 1 was filtered and water was removed. Then 10 mL of buffer solution (95% ethyl alcohol) was added and stirring was conducted for 8 h under heating. The product was centrifugally separated for 15 min at 10,000×g and the supernatant thereof was used as a sample.

2) Measurement of Water-Soluble Polyphenols

Similarly to the above-described Working Example 1, absorbance at each wavelength of 220 nm, 280 nm, and 550 nm was measured with a spectrophotometer.

Furthermore, the amount of polyphenols was determined by titration by using a phenol reagent and taking gallic acid as a standard. An average value was found for a total of ten measurements in the same manner as in Working Example 1. The results are shown in Table 3.

3) Results

In Comparative Example 3, water-insoluble polyphenols were extracted. The amount of polyphenols in the first day was large. However, it was confirmed to decrease with each passing day. This phenomenon can be considered as glycosidation of water-insoluble polyphenols and conversion thereof into water-soluble glycoside polyphenols.

TABLE 3

| Wavelength | 1 day | 2 days | 4 days | 7 days |
|---|---|---|---|---|
| A220 | 0.583 | 0.291 | 0.393 | 0.473 |
| A280 | 0.292 | 0.452 | 1.41 | 0.982 |
| A550 | 0.592 | 0.895 | 1.861 | 1.534 |
| Amount of polyphenols (mg/100 mL) | 10.9 | 18.3 | 36.6 | 30.2 |
| Amount of polyphenols obtained by ethanol extraction from residue (mg/100 mL) | 40.9 | 28.3 | 18.6 | 16.2 |

What is claimed is:

1. A method of preparing grape seeds for extraction, comprising:
    removing juice from the seeds;
    drying the grape seeds after removing the juice step;
    heating the grape seeds after the drying step so as not to sterilize the grape seeds; wherein the heating is carried out using a temperature range of 50-70° C.;
    hydrating the grape seeds with water;
    inducing germinating of the grape seeds, after the hydrating step by maintaining the grape seeds at a temperature range optimum for germination, until germination of the grape seeds occurs; and,
    extracting water soluble polyphenols from the geminated grape seeds after the germinating step, wherein the germinated grape seeds are crushed, mixed with water to create an emulsion and the water is evaporated from the emulsion to form a concentrate of water soluble polyphenols.

2. The method of preparing grape seeds for extraction, as recited in claim 1, wherein after the drying step, the grape seeds have a water content of 9-12%.

3. The method of preparing grape seeds for extraction, as recited in claim 1, wherein the hydrating step is after the heating step and after the hydrating step the grape seeds have a water content of at least 17 percent.

4. A method for extracting water soluble polyphenols from dried grape seeds comprising:
    inducing germination of the grape seeds by drying the grape seeds, then heating and hydrating the grape seeds to awaken the grape seeds from a dormant state and to increase the water content of the seed to at least 17 percent, wherein once the grape seeds are awakened, the grape seeds are maintained at a temperature range optimum for germination, which is 20 to 45 degrees centigrade or 50 to 70 degrees centigrade, until the grape seeds germinate; and, extracting the water soluble polyphenols from the germinated grape seeds, including crushing the germinated grape seeds, mixing the crushed grape seeds with water to create an emulsion and evaporating water from the emulsion.

5. The method extracting water soluble polyphenols from dried grape seeds, as recited in claim 4, wherein during the inducing germination step, when the grape seeds are dried, the grape seeds have a water content of 9-12%.

6. The method extracting water soluble polyphenols from dried grape seeds, as recited in claim 4, wherein during the inducing germination step, when the grape seeds are hydrated, the grape seeds have a water content of at least 17 percent.

* * * * *